(12) United States Patent
Farin (10) Patent No.: US 9,668,801 B2
(45) Date of Patent: Jun. 6, 2017

(54) METHOD AND DEVICE FOR OPERATING AN RF SURGICAL ASSEMBLY

(75) Inventor: Guenter Farin, Tuebingen (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 1237 days.

(21) Appl. No.: 13/229,425

(22) Filed: Sep. 9, 2011

(65) Prior Publication Data

US 2011/0319883 A1    Dec. 29, 2011

Related U.S. Application Data

(63) Continuation of application No. PCT/DE2010/075024, filed on Mar. 9, 2010.

(30) Foreign Application Priority Data

Mar. 10, 2009 (DE) .......................... 10 2009 012 431

(51) Int. Cl.
| | |
|---|---|
| *A61B 18/18* | (2006.01) |
| *A61B 18/12* | (2006.01) |
| *A61B 18/00* | (2006.01) |
| *A61B 18/16* | (2006.01) |
| *A61B 18/14* | (2006.01) |

(52) U.S. Cl.
CPC .......... *A61B 18/1206* (2013.01); *A61B 18/16* (2013.01); *A61B 2018/00726* (2013.01); *A61B 2018/00857* (2013.01); *A61B 2018/1407* (2013.01)

(58) Field of Classification Search
CPC ................ A61B 18/1206; A61B 18/16; A61B 2018/1407; A61B 2018/00875; A61B 2018/00726

USPC .......................................... 606/37, 41, 42, 50
See application file for complete search history.

(56) References Cited

U.S. PATENT DOCUMENTS

| | | | |
|---|---|---|---|
| 4,244,371 A | 1/1981 | Farin | |
| 5,078,716 A | 1/1992 | Doll | |
| 6,113,596 A | 9/2000 | Hooven et al. | |
| 6,540,695 B1 * | 4/2003 | Burbank | A61B 10/0266 600/564 |
| 2001/0044625 A1 * | 11/2001 | Hata | A61B 18/1492 606/41 |

(Continued)

FOREIGN PATENT DOCUMENTS

| | | |
|---|---|---|
| DE | 2132808 A1 | 1/1973 |
| DE | 7418576 U | 9/1974 |

(Continued)

OTHER PUBLICATIONS

International Search Report; Application No. PCT/DE2010/075024; Issued: Aug. 31, 2010; 3 pages.

*Primary Examiner* — Edward Moran
*Assistant Examiner* — Pamela M Bays
(74) *Attorney, Agent, or Firm* — Whitmyer IP Group LLC (57) ABSTRACT

A method and device for operating an RF surgical assembly for the RF surgical removal of pathological tissue in hollow organs of a patient wherein the RF surgical assembly includes an RF surgical device having an RF generator for generating an RF current and a bipolar loop having two mutually insulated loop sections which can be brought electrically in contact with the tissue and wherein the RF generator has a first and an antipolar second output.

13 Claims, 3 Drawing Sheets

(56) References Cited

U.S. PATENT DOCUMENTS

| | | | |
|---|---|---|---|
| 2002/0138075 A1* | 9/2002 | Edwards | A61B 18/1477 606/41 |
| 2006/0116675 A1* | 6/2006 | McClurken et al. | 606/51 |
| 2008/0208185 A1* | 8/2008 | Fischer et al. | 606/37 |
| 2008/0287948 A1* | 11/2008 | Newton et al. | 606/50 |

FOREIGN PATENT DOCUMENTS

| | | |
|---|---|---|
| DE | 2514501 A1 | 10/1976 |
| DE | 3220940 A1 | 12/1983 |
| DE | 10028413 A1 | 9/2001 |
| DE | 10253819 A1 | 7/2004 |
| DE | 102007008272 A1 | 8/2007 |
| EP | 0390937 A1 | 10/1990 |

* cited by examiner

METHOD AND DEVICE FOR OPERATING AN RF SURGICAL ASSEMBLY

CROSS-REFERENCE TO RELATED APPLICATIONS

This application is a continuation of pending International Application PCT/DE2010/075024 filed on Mar. 9, 2010, which designates the United States and claims priority from German Patent Application No. 10 2009 012 431 filed on Mar. 10, 2009.

FIELD OF THE INVENTION

The invention relates to a method and device suitable for this purpose for operating an RF surgical assembly, including bipolar RF surgical instruments, in particular bipolar loops by which means pathological tissue in hollow organs or body cavities can be ensnared under endoscopic control and removed by RF surgery.

BACKGROUND OF THE INVENTION

Pathological tissue in hollow organs means here in particular tumors of the mucosa (mucous membrane) of the gastro-intestinal tract, taking into account a possible invasion into the submucosa located thereunder. Known methods by which means pathological mucosa can be ensnared under endoscopic control by means of instruments suitable for this purpose and removed or ectomised or resected by RF surgery are polypectomy as well as mucosectomy or mucosal resection. Polypectomy can be used when the pathological tissue protrudes from the normal mucosal level (generally called polyp) and can be ensnared with an instrument available for this purpose and thus can thus be removed by RF surgery. If a pathological mucosal area does not protrude sufficiently far from the adjoining mucosal level so that it can be ensnared with an available instrument, it can be raised out from the adjoining mucosal level (generally called pseudo-polyp), for example, by injecting normal saline solution into the submucosa located thereunder, sufficiently far that it can be ensnared like a polyp and removed. This method is called mucosectomy or mucosal resection. The common purpose of this method is the complete removal of pathological mucosa and the submucosa located thereunder. This purpose is achieved when the pathohistological examination of the removed tissue confirms that the criteria of a RO resection are satisfied, that is, the ectomy or resection has been made in healthy tissue outside the pathological tissue so that one can be sure that the entire pathological tissue has been removed.

RF surgical instruments available for this purpose, in particular for endoscopic polypectomy in the gastro-intestinal tract, are so-called polypectomy loops. Both the loop-shaped electrodes in general and also (pars pro toto) the complete RF surgical instruments including the loop-shaped electrodes are designated by "polypectomy loop". Since these instruments are not only suitable for the ectomy of polyps but also for the ectomy of other pathological tissue, for example, for the ectomy of a major duodenal papilla (papillectomy), for the ectomy or resection of pathological mucosal areas (mucosectomy or mucosal resection) etc., hereinafter the loop-shaped electrodes per se and where generally valid are called "loop" for short, the entire instruments including loop, where generally valid is called "instrument" for short, the polyps, papillae, pathological mucosal areas etc., where generally valid are called "target tissue" for short and the ectomisation or resection etc., where generally valid is called "removal" for short (removal includes cutting and coagulating or thermal haemostasis).

Figure 6:
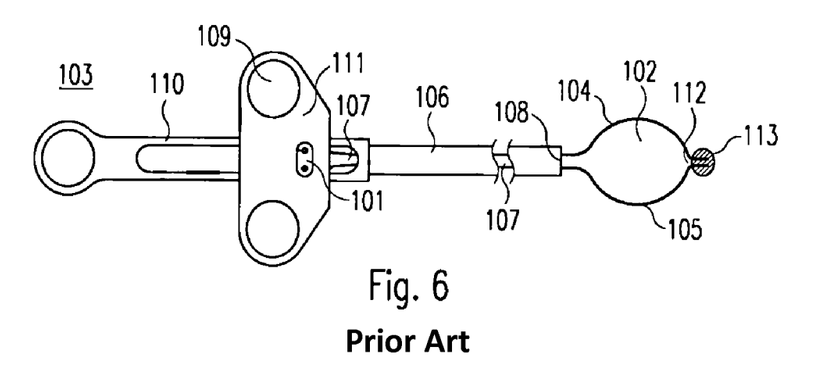
FIG. 6 shows an RF surgical instrument according to the prior art.

As shown schematically in FIG. 6, known instruments substantially include a loop 102, a flexible catheter 106, at least one flexible but sufficiently stiff manipulation wire 107 which is used inside the catheter for pushing out and pulling in the loop in the axial direction from or into the distal end 108 of the catheter 106 and for conducting the RF current required for the RF surgical removal of target tissue, and a handle 109 at the proximal end of the catheter which consists of a slide rail 110 and a slider 111 for the manual pushing out or pulling in of the loops from or into the distal end of the catheter. At least one electrical contact for the connection of an RF surgical generator (RF generator) is disposed on the slider. Bipolar loops are, for example, separated at their distal end 112 into two electrically separated loop sections and are mechanically interconnected by means of an electrically insulating connecting element 113.

With regard to the application of the RF current, a distinction is made between so-called monopolar methods and loops suitable for this, e.g. DE 2132808 and so-called bipolar methods and loops suitable for this, e.g. DE 102007008272 or DE 3220940.

Monopolar loops are characterized in that their RF-surgically effective sections can only be connected to one pole of an RF generator whilst the other pole of the RF generator must be connected to the patient via a neutral electrode. The RF current flows between loop and neutral electrode through the patient, i.e. not only through the target tissue but also through other tissue or tissue collateral to the target tissue. Monopolar loops exist today in various forms, with these however having no intentional influence on the RF surgical effects during the removal of target tissue but are intended to be used for mechanical manipulation or application according to the various localizations, sizes and/or shapes of the target tissue.

For more than 30 years ago now, it has been pointed out that when using monopolar loops, thermal damage to collateral tissue can be caused by the RF current flowing uncontrolledly between loop and the neutral electrode required in the monopolar method. Solutions to obviate this problem have been sought for just as long and again and again bipolar loops have been suggested as the solution in this respect.

Bipolar loops are characterized in that the loop, as for example that according to DE-G 7418576, is divided into two equal-length and mirror-symmetrically shaped loop sections (generally called symmetrical bipolar loop) or, as for example, that according to DE 3220940, into two different-length and generally asymmetrically shaped loop sections (generally called asymmetric bipolar or quasi-bipolar loops) and these loop sections are mechanically interconnected at their distal end by means of an element which electrically insulates the loop sections from one another. One of the two loop sections is connected to one pole and the other loop section is connected to the other pole of an RF generator. In this bipolar operating mode the RF current predominantly flows between the two loop sections through the tissue located between these loop sections. In symmetrical bipolar loops both loop sections should act as active electrodes. In asymmetric bipolar loops the shorter loop section should act as an active electrode and the longer loop section as a neutral electrode. A separate neutral electrode is consequently not necessary to operate a symmetrical or asymmetric bipolar loop. Accordingly, bipolar loops are connected to both poles of an RF generator so that the automatic monitoring of the connection of a neutral electrode to the RF generator prescribed in RF generators for monopolar operation and their application to the patient is not necessary or is disabled.

Bipolar loops or the bipolar operation of so-called bipolar loops has not, however, proved successful in clinical application. One reason for this is the electrical insulation sections at the proximal and at the distal end between the two loops sections. For RF surgical cutting the amplitude of the RF voltage between an active electrode used for cutting and the tissue to be cut must reach at least 200 Volts. Since in bipolar instruments at least 200 Volts having opposite polarity or phasing must be achieved simultaneously at each of the two active electrodes, the electrical insulation sections between the two active electrodes in particular at the proximal and at the distal end of the loop, where the distances between the two electrodes are very short, must withstand a voltage amplitude or amplitude difference of at least 400 V. If electrical arcs are formed between the two electrodes at these points, these electrodes can then melt as a result of the high temperature of these electrical arcs. According to DE 2514501, this problem should be solved by partial electrical insulation of the two loop sections which, however is not achieved or cannot be achieved at the distal end of the bipolar loop shown there.

Since the introduction of endoscopic polypectomy and mucosectomy, endoscopists would like to remove increasingly larger polyps or pathological mucosal/submucosal areas, in particular in the gastro-intestinal tract, for diagnostic and/or therapeutic purposes and this with a view to the pathohistological examination as far as possible in toto and as radically as possible to avoid recurrences. Radically means here including the submucosa of the affected mucosal area to as close as possible to the muscularis propria. As the size of the polyps ectomised in toto and radically or resected mucosal/submucosal area increases, however, when using hitherto available polypectomy or mucosectomy loops, the resulting complications and problems, especially bleeding and perforations also increase. In addition, only polyps or mucosal/submucosal areas up to about 2 mm diameter can be removed in toto with this method and the polypectomy or mucosectomy loops hitherto available for this purpose and the RF generators available for this purpose. Larger polyps or mucosal/submucosal areas can only be removed by this method in several smaller portions, the so-called piecemeal technique, and frequently are not removed radically or completely, which makes the pathohistological examination of the tissue thus removed and the allocation of a positive pathological finding to the respective resection site difficult or even impossible. In addition, tumors not removed completely can grow further.

Although polypectomy and mucosectomy are considered to be clinically established methods for the prophylaxis of malignant and especially metastasizing tumors, apart from the complications already specified above, these methods are beset with problems which also correlate with the size of the target tissue.

One of these problems, especially in the case of large polyps and/or sessile (flat growing) polyps as well as mucosal/submucosal areas which become large or even larger than they already are due to submucosal injection, are the electrical power or RF voltage and RF current required for their removal in toto. Since the RF surgical cutting effect can only occur when a vapor layer is present between the loop used for the cutting and the tissue to be cut, so that electric arcs are formed at sufficiently high RF voltages which burn away (pyrolysis effect) the tissue located near the loop, the tissue near the loop must be heated to the boiling point of water. If the heating of this tissue takes place too slowly and the cutting effect is consequently time-delayed (first cut delay), during the first cut delay the heat can diffuse from the near-loop tissue into adjacent tissue and damage this thermally. Thermal damage to the muscularis propria or even the serous membrane of an organ of the gastro-intestinal tract usually results in a perforation of the organ wall.

An RF current of at least 0.5 Ampere per cm of loop length is required for a sufficiently delay-free first cut in polypectomy or mucosal resection. Since RF generators of known RF surgical devices generate a maximum of 1.5 to 3 Amperes, only polyps having a diameter in the application range of the loop of about 1 to 2 cm, which corresponds to a loop length of about 3 to 6 cm, can be removed in toto with a sufficiently small first cut delay. In the case of larger polyps, the cutting effect is completely absent.

In order to reduce the RF current required for cutting and therefore to avoid a first-cut delay, it is proposed in DE 100 28 413 A1 to delimit the effective electrode surface of a monopolar loop electrode of the known type to a partial area in the vicinity of the electrode tip by means of an insulating sheathing of the two loop sections. The teaching according to DE 100 28 413 A1 substantially consists in concentrating, by means of a constructive measure, the effective electrode surface of the loop element only onto that surface region of the loop electrode on which the thermal cutting process of the loop electrode produced by the electrosurgical current flow should ideally take place. This constructive delimitation of the effective electrode surface by means of an at least partial insulation of the two loop sections should allegedly substantially simplify the handling of the electrosurgical instrument since the risk of miscuts or undesired contacts with healthy neighboring tissue is reduced to a minimum. The latter, however, only applies when the partial areas in the vicinity of the electrode tip are insulated partially on their circumference and/or at their tip, as is described for example in this DE 100 28 413 A1, which however can be disturbing or even obstructive during cutting guidance. A substantial disadvantage of the partial insulation of the circumference from partial areas of the loop, however, is the low efficiency of the coagulation or the thermal haemostasis.

DE 25 14 501 describes a bipolar coagulation instrument for endoscopes for the removal of polyps, for example, in the stomach, where a high-frequency current for haemostasis is fed to the electrodes and which is characterized in that the two electrodes form a loop whereby they are interconnected at their ends by means of an insulation piece. One embodiment of this coagulation instrument is characterized in that the electrodes are provided with an insulating layer over their entire length with the exception of an area in the vicinity of the insulation piece. When applying such a bipolar coagulation instrument, there should certainly be no first-cut delay but insulation problems in the area of the insulation piece when polyps are to be cut away by RF surgery using this coagulation instrument, for which RF voltages having amplitudes of at least 400 V are required. For coagulation or haemostasis, the partial insulation of the electrode on the circumference of the ends of the electrodes is rather disadvantageous because the effective contact areas are very narrow as a result.

U.S. Pat. No. 5,078,716 describes a monopolar polypectomy loop whose two loop sections are electrically insulated proximally apart from relatively short sections at their distal ends so that only a relatively short section at the distal end of the loop is uninsulated and thereby RF surgically effective. Such loops certainly require less RF current than equal-sized loops without insulation but have the disadvantage that the surgically effective part of the loop from the perspective of an endoscope is always behind the polyp, that is out of visual control, and there is the risk that in particular the distal tip of the loop can uncontrollably perforate especially thin-walled organs. Among other things, the subject matter of DE 100 28 413 A1 is to avoid the latter.

Both in electrosurgical instruments according to U.S. Pat. No. 5,078,716, DE 100 28 413 A1 and also in coagulation instruments according to DE 25 14 501, the RF surgically effective electrode surfaces are only disposed at the distal end of the loop with the disadvantage that these are always behind the tissue to be removed from the viewing direction of an endoscope and consequently become active without visual control.

A further problem is that large target tissue cannot be removed in toto but only in several smaller portions (piecemeal technique) from an organ wall using hitherto available loops and RF generators. At the present time various endoscopic submucosal dissection (ESD) methods are being developed for the in toto removal of larger mucosal/submucosal areas and some are already being used clinically. A common feature of these ESD methods is the RF surgical preparation of the relevant mucosal/submucosal area near the muscularis propria, for example, using a needle electrode. These methods require a high manual dexterity, experience, continuous training, willingness to take risks and a large amount of time. So far there are only a few experts practicing these methods.

To sum up, it can be noted with regard to the prior art here that many differently designed loops are now available or have at least been proposed for the endoscopic removal of target tissue (see above) but so far none is suitable for removing sufficiently reliably larger target tissue in toto, in particular larger than 2 cm in diameter.

SUMMARY OF THE INVENTION

The embodiments are based on the object of providing RF surgical methods and devices suitable for this purpose for the endoscopically controlled removal of pathological tissue, in particular the mucosa and submucosa of the gastro-intestinal tract, during the application whereof the problems listed above are less present or not present at all and with which in particular even larger tissue areas than about 2 cm in diameter can be removed in toto and as radically as possible from organ walls, for which the piecemeal technique, endoscopic submucosal dissection (ESD) or open surgery have previously been reserved.

The object is achieved in terms of the method whereby so-called bipolar loops, i.e. loops having two mutually insulated loop sections, are applied but these can be operated not only in bipolar mode but alternatively or alternatingly also in monopolar mode, whereby only one or simultaneously both of the two loop sections is or are alternatively or alternatingly connected to one pole of an RF generator as active electrode whilst the other pole of the RF generator is connected to a neutral electrode applied to the patient.

In particular, this object is achieved in regard to the method by the subject matter of claim 1 and in regard to the device by the subject matter of claim 8.

The embodiments are based on the idea of providing a method for operating an RF surgical assembly for the RF surgical removal of pathological tissue in hollow organs of a patient, e.g. of polyps in the gastro-intestinal tract, where the RF surgical assembly includes an RF surgical device having an RF generator for generating the RF current required for this purpose and a bipolar loop having two mutually insulated loop sections which can be brought electrically in contact with the tissue and where the RF generator has a first and an antipolar second output. According to a first embodiment, in a bipolar mode respectively one of the outputs is connected to respectively one loop section and in a monopolar mode the first output is connected to a neutral electrode which can be attached to the patient and the second output is connected to at least one loop section, where furthermore a monopolar mode is set at least temporarily, in which only one of the two loop sections is connected to the second output.

The monopolar operation of a bipolar loop with only one loop section as the active electrode enables the removal of large polyps or mucosal-submucosal areas in toto, which cannot be removed in toto with monopolar loops and this in addition without first cut problems and without overloading the electrical insulation sections between the two loop sections. In the case of very large polyps or mucosal-submucosal areas, preferably asymmetric bipolar loops can be used, with preferably the shorter loop section in each case being used as active electrode.

The monopolar operation of a bipolar loop with simultaneously both loop sections as active electrode allows the removal of polyps or mucosal-submucosal areas which can also be removed with monopolar loops in toto and without first cut problems. The application of bipolar instead of monopolar loops can nevertheless be advantageous in these cases if the procurement and provisioning costs for a hospital can thereby be reduced by restricting to the smallest possible types of loops.

Furthermore the alternative monopolar operation of bipolar loops offers further advantages compared with both known partially insulated and also conventional non-partially insulated loops such as, for example, better controllability of the cutting direction, better endoscopic view of the RF surgically active loop sections and in particular the possibility of making the RF surgical cut in monopolar mode using only one or both of the two loop sections and performing the thermal haemostasis, generally called coagulation, in bipolar mode between two loop sections, where the bipolar coagulation can be carried out using so-called soft coagulation, which is characterized in that the amplitude of the RF voltage required for this purpose is less than 200 Volts, so that the critical insulation sections of bipolar loops are not overloaded.

However, the method is not applicable using hitherto available devices and/or RF surgical equipment. Hitherto available RF surgical devices do have at least one connecting socket for the monopolar operation of monopolar instruments including monopolar loops and/or at least one connecting socket for the bipolar operation of bipolar instruments including bipolar loops, but no connecting socket for the monopolar operation of bipolar loops.

The embodiments are also based on the idea of providing a device for operating an RF surgical assembly for the RF surgical removal of pathological tissue in hollow organs of a patient, e.g. of polyps in the gastro-intestinal tract, where the RF surgical assembly includes an RF surgical device having an RF generator for generating the RF current required for this purpose and a bipolar loop having two mutually insulated loop sections which can be brought electrically in contact with the tissue and where the RF generator has a first and an antipolar second output. The device thereby includes adapter, switch and/or double-throw switch or similar switchover device, which in a bipolar mode connects respectively one of the outputs to respectively one loop section and which in a monopolar mode connects the first output to a neutral electrode which can be attached to the patient and connects the second output to at least one loop section and which is furthermore configured in such a manner that a monopolar mode can be set at least temporarily, in which only one of the two loop sections is connected to the second output.

The device according to an embodiment for the monopolar or both for the monopolar and for the bipolar operation of so-called bipolar loops, i.e. loops having two loop sections which are electrically insulated from one another, preferably includes electrical connecting elements, in particular pluggable and/or switchable electrical contact elements, with the result that for the monopolar operation of bipolar loops only one or alternatively or alternatingly one or the other or simultaneously both loop sections can be connected jointly to one of the two poles of an RF generator of an RF surgical device and the other pole of the RF generator of an RF surgical device, as is usual in monopolar operating modes, can or will be connected by connecting elements to a neutral electrode or with the result that alternatively to or alternating with at least one of the monopolar operating modes listed above, for the bipolar operation of bipolar loops, one pole of the RF generator can or will be connected to one loop section and the other pole of the RF generator can or will be connected to the other loop section instead of to a neutral electrode.

BRIEF DESCRIPTION OF THE DRAWINGS

In the following, the invention will be described by way of example, without limitation of the general inventive concept, on examples of embodiments and with reference to the drawings. Elements which are identical or which have the same effect are characterized by identical reference numbers. In the figures

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Figure 1:
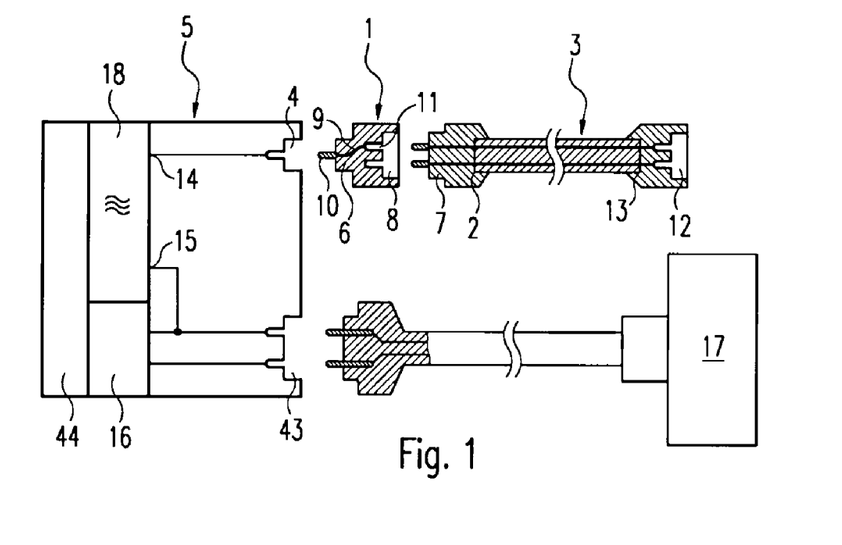
FIG. 1 shows an adapter for the monopolar operation of bipolar loops.

FIG. 1 shows a first exemplary embodiment for the monopolar operation of so-called bipolar loops 103, i.e. loops having two loop sections 104, 105 which are electrically insulated from one another, includes electrical connecting elements, whereby for the monopolar operation of these loops 103, respectively only one of the two loop sections 104, 105 can be connected to one of the two outputs 14, 15 of an RF generator 18, and the other output 14, 15 of the RF generator 18 when using this device as usual in monopolar operating modes can or must be connected to a neutral electrode 17 in a known manner.

A device according to this exemplary embodiment can, as shown schematically in FIG. 1, include an adapter 1 which, for example, can be inserted between the proximal end 2 of a bipolar connecting cable 3 for bipolar loops 103 or instruments, and a monopolar connector socket 4 of an RF surgical device 5. The adapter 1 includes two connecting elements and specifically one for the monopolar connector plug 6 compatible with the monopolar connector socket 4 of the RF surgical device 5 and one bipolar connector socket 8 compatible with the bipolar connector plug 7 at the proximal end 2 of the bifilar or bipolar connecting cable 3. An electrically conductive bridge 9 connects a first contact element 10 of the monopolar connector plug 6 to a second contact element 11 of the bipolar connector socket 8.

The connecting elements, in particular the bipolar connector plug 7 and the bipolar connector socket 8 between one such adapter 1 and a bipolar connecting cable 3 and/or a further bipolar connector socket 12 at the distal end 13 of the bipolar connecting cable 3 and the bipolar plug contact 101 of bipolar loops 103 or instruments (see FIG. 6) can be configured such that exclusively only one or alternatively one or the other of the two loop sections 104, 105 can be connected to one of the two outputs 14, 15 of the RF generator 18 of the RF surgical device 5, for example, by configuring the plug-in direction of the bipolar connector plug 7 at the proximal end 2 and/or distal end 13 of the bipolar connector cable 3 to be fixed or variable. This aspect is particularly relevant when using asymmetric bipolar loops 103. When using asymmetric bipolar loops 103, it is particularly expedient for the in toto removal of very large target tissue to use the respectively shorter loop section 104, 105 as the active electrode.

The device is consequently characterized by the fact that it can exclusively connect only one or alternatively one or the other of the two loop sections 104, 105 of a bipolar loop 103 to the output 14, 15 of an RF generator to which monopolar active electrodes or loop sections 104, 105 can be connected as intended in the monopolar operating mode. When using asymmetric bipolar loops 103, it is particularly expedient for the in toto removal of very large target tissue to use the respectively shorter loop section 104, 105 as the active electrode. Unlike the bipolar operation of a bipolar loop 103, in the monopolar operation of a bipolar loop 103, a neutral electrode 17 must be connected to the first output 15 of the RF generator 18 and also applied to the patient when using this device and this is monitored by an automatic safety device 16 usual for this purpose, which is included as prescribed in RF surgical devices 5 and therefore not presented and described in detail, for example, in accordance with EP 0 390 937.

Figure 2:
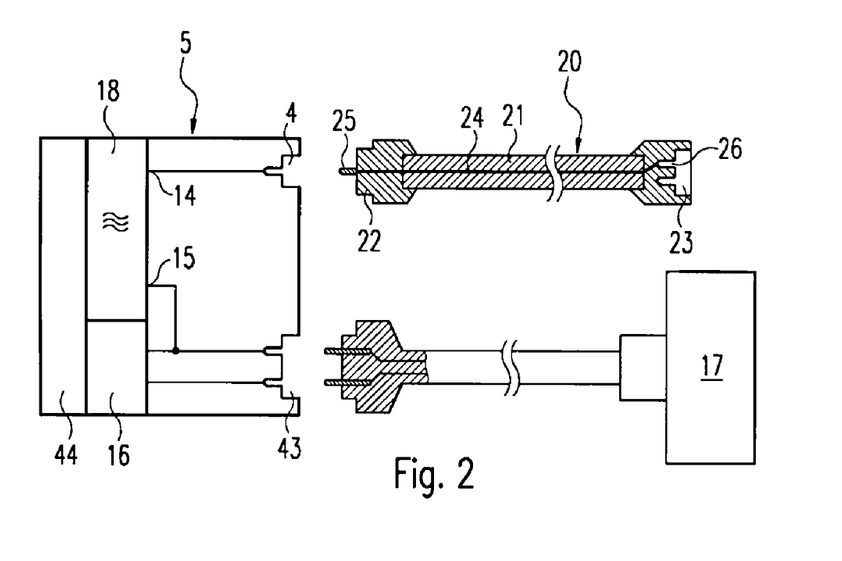
FIG. 2 shows an adapter cable for the monopolar operation of bipolar loops.

A second exemplary embodiment of a device for the monopolar operation of so-called bipolar loops 103, i.e. loops 103 having two loop sections 104, 105 which are electrically insulated from one another, includes electrical connecting elements, whereby for the monopolar operation of these loops 103, only one of the two loop sections 104, 105 can be connected to one of the two outputs 14, 15 of an RF generator 18 of an RF surgical device 5, and the other output 15, 14 of the RF generator 18 when using this device as usual in monopolar operating modes can or must be connected to a neutral electrode 17 in a known manner.

A device according to this exemplary embodiment can, as shown schematically in FIG. 2, include a further adapter or an adapter cable 20 which, for example, can be inserted as extension cable between the proximal end 2 of a usually bifilar, so-called bipolar connecting cable 3 for bipolar loops 103 or the bipolar plug contact 101 of a bipolar loop 103 or of a bipolar instrument and a monopolar connector socket 4 of an RF surgical device 5. The adapter cable 20 includes one cable section 21 having one electrical connecting element at the ends thereof, and specifically one connector plug 22 compatible with the monopolar connector socket 4 of the RF surgical device 5 and one connector socket 23 compatible with the bipolar connector plug 7 at the proximal end 2 of the bipolar connecting cable 3 or compatible with the bipolar plug contact 101 directly at the bipolar loop 103 or on the bipolar instrument. An electrically conductive core 24 of the adapter cable 20 connects a first contact element 25 of the connector plug 22 to a contact element 26 of the connector socket 23 of this adapter cable 20.

If the plug-in direction between the connector socket 23 at the distal end of the adapter cable 20 and the bipolar connector plug 7 at the proximal end 2 of the bipolar connecting cable 3, which can be used as extension cable, is variable, the one or the other loop section 104, 105 can then be connected alternatively to the second output 14 of the RF generator 18 which can be advantageous particularly when using asymmetric bipolar loops 103.

The device is consequently characterized by the fact that it can exclusively connect only one or, if the plug-in direction of at least one plug connection, in particular between the bipolar connector plug 7 or the bipolar plug contact 101 and the connector socket 23, is variable, alternatively one or the other of the two loop sections 104, 105 of a bipolar loop 103 to the second output 14, 15 of an RF generator 18 to which monopolar active electrodes can be connected in the monopolar operating mode. Unlike the bipolar operation of a bipolar loop 103, in the monopolar operation of a bipolar loop 103, as already noted above in the first exemplary embodiment, in the monopolar operation of a bipolar loop 103, a neutral electrode 17 must be connected to the first output 15 of the RF generator 18 and also applied to the patient when using this device and this is monitored by an automatic safety device 16 usual for this purpose and therefore not presented and described in detail.

The exemplary embodiments of devices for the alternative monopolar operation of bipolar loops 103 described above with reference to FIG. 1 and FIG. 2 are particularly suitable for the many RF surgical devices 5 already in existence which still have no device for the monopolar operation of only one of the two loop sections 104, 105 of bipolar loops 103. Naturally, a bipolar connector socket 8 compatible with the bipolar connector plug 7 or connection plug 22 of the bipolar connecting cable 3 or the adapter cable 20 can be an integral component of an RF surgical device 5, where however for the monopolar operation of bipolar loops 103, only one of the two outputs 14, 15 the RF generator 18 may be connected to one or both contacts of this connector socket 8 and in addition, a neutral electrode 17 required for monopolar operation must be applied to the patient and connected to the RF generator 18. RF surgical devices 5 which are already equipped with a bipolar connector socket 8 compatible with bipolar connecting cables 3 for the bipolar operation of bipolar loops 103, can however not only be modified for the monopolar operation of bipolar loops 103 by one of the two outputs 14, 15 of the RF generator 18 being separated from this bipolar connector socket 8. Known RF surgical devices 5 having integrated bipolar connector sockets 8 for bipolar loops 103 or instruments are specifically characterized in that in the bipolar operating mode the automatic monitoring of the connection of a neutral electrode 17 at the RF generator 18, as prescribed in RF surgical devices 5, and furthermore the automatic monitoring of the application of neutral electrodes 17 on the patient is deactivated.

Figure 3A:
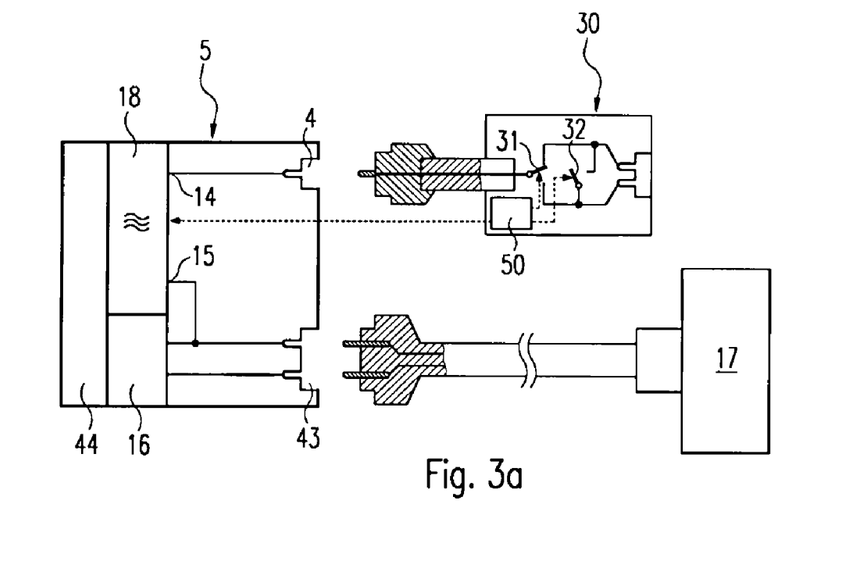
FIG. 3a shows a switchover device for the monopolar operation of bipolar loops.

A third exemplary embodiment of a device for the monopolar operation of so-called bipolar loops 103, i.e. loops 103 having two loop sections 104, 105 which are electrically insulated from one another, includes electrical connecting elements, whereby for the monopolar operation of these loops 103, alternatively or alternatingly one or the other of the two loop sections 104, 105 or alternatively or alternatingly one or the other or both of the loop sections 104, 105 simultaneously can be connected to one of the two outputs 14, 15 of an RF generator 18, and the other output 15, 14 of the RF generator 18 when using this device as usual in monopolar operating modes can or must be connected to a neutral electrode 17 in a known manner.

Figure 3B:
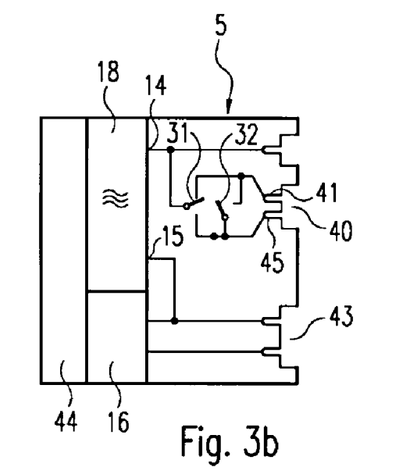
FIG. 3b shows an RF surgical device having a device for the monopolar operation of bipolar loops.

A device according to this exemplary embodiment can, for example, as shown schematically in FIG. 3*a*, include a switchover device 30 and be used as intended as a switch box or, as shown schematically in FIG. 3*b*, it can be an integral component of an RF surgical device 5. In the form of a switchover device 30, this exemplary embodiment differs compared with the first exemplary embodiment in that additionally a first double-throw switch 31 is provided, by which means alternatively or alternatingly one or the other loop section 104, 105 of a bipolar loop 103 can be connected to the second output 14 of the RF generator 18. The switchover device 30 can additionally include a switch 32 by which means the two loop sections 104, 105 can be electrically interconnected.

Figure 4:
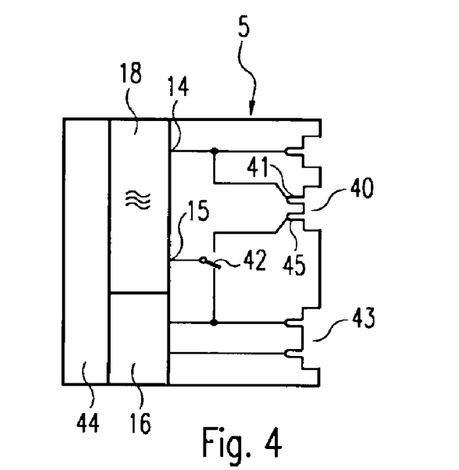
FIG. 4 shows an RF surgical device having a device for the monopolar or bipolar operation of bipolar loops.

A fourth exemplary embodiment of a device according to the invention that is alternatively or alternatingly suitable both for the monopolar operation and also for the bipolar operation of so-called bipolar loops 103, i.e. loops having two loop sections 104, 105 which are electrically insulated from one another, includes electrical connecting elements for the electrically conductive connection of one output 14, 15 of the RF generator 18 to one of the two loop sections 104, 105 and a first double-throw switch 31 for the alternative or alternating connection of the other output 15, 14 of the RF generator 18 to the other of the two loop sections 104, 105 or to a neutral electrode 17.

A switch box or a switchover device 30 according to this exemplary embodiment can, in accordance with FIG. 3*a*, be used on RF surgical devices 5 without means for the monopolar operation of bipolar loops 103 but is more advantageously an integral component of an RF surgical device 5 and is therefore only presented and described in this embodiment by reference to FIG. 4. It is certainly possible for a person skilled in the art in this field to also implement this embodiment in the form of a switch box or similar.

As an integral component of an RF surgical device 5, this exemplary embodiment, as shown schematically in FIG. 4, substantially includes a bipolar additional socket 40 compatible with the bipolar connector plug 7 on the proximal end 2 of the bipolar connecting cable 3, whose first contact 41 is permanently connected to the second output 14 of the RF generator 18, and a second double-throw switch 42 by which means the first output 15 of the RF generator 18 can alternatively or alternatingly be connected to the other of the two loop sections 104, 105 or to a neutral electrode 17 connected to a neutral connector socket 43. This exemplary embodiment can also only be used as intended when a neutral electrode 17 is connected to the RF surgical device 5 and applied to the patient. If the RF surgical device 5 is fitted with a safety device 16 for the automatic monitoring of the connection of a neutral electrode 17 at the RF surgical device 5 and/or the application of the neutral electrode 17 on the patient, then this safety device 16 cannot be used without or with an inadequately applied neutral electrode 17.

Figure 5:
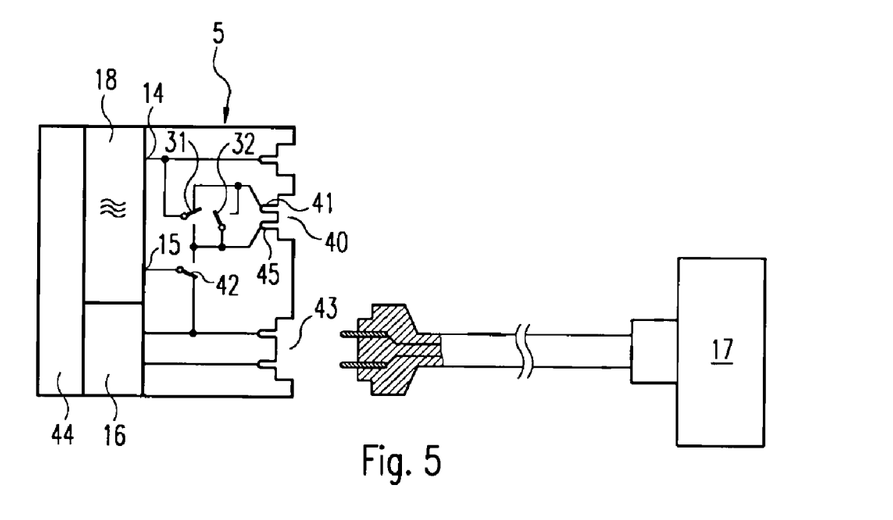
FIG. 5 shows an RF surgical device having a device for the monopolar or bipolar operation of bipolar loops.

A fifth exemplary embodiment of a device that is suitable for monopolar operation and also for both monopolar and bipolar operation of so-called bipolar loops 103, i.e. loops having two loop sections 104, 105 which are electrically insulated from one another, includes electrical connecting elements whereby for the monopolar operation of bipolar loops 103, one of the two outputs 14, 15 of an RF generator 18 can be connected to only one or alternatively or alternatingly to one or the other or simultaneously to both of the two loop sections 104, 105 jointly, and the other output 15, 14 of the RF generator 18 can be connected alternatively or alternatingly to the other of the two loop sections 104, 105 or to the neutral electrode 17.

This fifth exemplary embodiment shown in FIG. 5 is substantially a combination of the exemplary embodiments presented and described above with reference to FIG. 3b and FIG. 4 and contains no additional connecting elements to the exemplary embodiments presented and described above with reference to FIG. 3b and FIG. 4. For a person skilled in the art in this field a description of this exemplary embodiment with reference to FIG. 5 would be a repetition of the descriptions of the third and fourth exemplary embodiment.

However, further embodiments of these devices, in particular in relation to their function and suitability for use are described hereinafter with reference to the fifth exemplary embodiment shown in FIG. 5 and this applies additionally for the exemplary embodiments already described above with reference to FIG. 3b and FIG. 4.

One embodiment of the exemplary embodiment shown in FIG. 3b and FIG. 4 and in particular the combination thereof shown as a fifth exemplary embodiment in FIG. 5 consists in that the switchable connecting elements, i.e. in particular switch 32 and double-throw switches 31, 42, are electromechanical relays or semiconductor switches whose switching positions can be configured electronically alternatively or alternatingly and this in particular by storable or stored programs and electronic control devices 50 sufficiently known to an average person skilled in the art in this field, for example, by an electronic computer or a CPU 44. This embodiment is very advantageous for applications of these devices as intended, for example, for the endoscopically controlled removal of polyps or pathological mucosal-submucosal areas from thin-walled hollow organs, which are in particular large and consequently liable to complications, insofar as the removal of such target tissue includes several different phases with specific requirements in regard to the thermal effects required in each case, for which the rapid sequence in time cannot be controlled by manual modification of the connecting elements.

In addition, in particular devices according to the fifth exemplary embodiment or FIG. 5 can be operated very advantageously with special operating modes or programs, for example, in accordance with DE 35 30 335 for polypectomy in such a manner that the configuration of the electromechanically switchable connecting elements is automatically synchronized, for example, with the alternating cutting and coagulation phases. For example, cutting phases can be applied cyclically in an alternating manner and in monopolar mode using one and/or the other of the two loop sections 104, 105 and coagulation phases either in monopolar mode using one and/or the other of the two loop sections 104, 105 or in bipolar mode with soft coagulation between both loop sections 104, 105 of bipolar loops 103.

As shown schematically in FIG. 6, instruments from prior art substantially include a loop 102, a flexible catheter 106, at least one flexible but sufficiently stiff manipulation wire 107 which is used inside the catheter for pushing out and pulling in the loop in the axial direction from or into the distal end 108 of the catheter 106 and for conducting the RF current required for the RF surgical removal of target tissue, and a handle 109 at the proximal end of the catheter which consists of a slide rail 110 and a slider 111 for the manual pushing out or pulling in of the loops from or into the distal end of the catheter. At least one electrical contact for the connection of an RF surgical generator (RF generator) is disposed on the slider. Bipolar loops are, for example, separated at their distal end 112 into two electrically separated loop sections and are mechanically interconnected by means of an electrically insulating connecting element 113.

It will be appreciated to those skilled in the art having the benefit of this disclosure that this invention is believed to provide means, components, assemblies and methods used for RF surgery. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for RF surgical removal of pathological tissue in hollow organs of a patient, comprising the steps of:
providing an RF generator configured to generate an RF current, wherein the RF generator has a first output and an antipolar second output;
providing a bipolar loop having first and second mutually insulated loop sections which can be brought electrically in contact with the patient;
providing a switchover device operable to switch the RF generator between a bipolar mode and a monopolar mode;
operating the assembly in the bipolar mode, in which the first output is connected to the first loop section, and the second output is connected to the second loop section such that the RF current flows through the first output and the first loop section, through the patient, and through the second loop section to the second output;
operating the assembly in the monopolar mode, in which the first output is connected to at least one of the first loop section and the second loop section; and the second output is connected to a neutral electrode which is configured to be attached to the patient, such that the current flows through the first output and the at least one of the first loop section and the second loop section, through the patient, and out the neutral electrode to the second output; and switching the operation of the RF generator between the bipolar and the monopolar mode at least temporarily.

2. The method of claim 1, wherein the second output is connected to one of the first loop section and the second loop section alternatively in a manner which is configured to be set by the operator.

3. The method of claim 1, wherein the second output is connected to one of the first loop section and second loop section in an automatically alternating manner.

4. The method of claim 1, wherein alternatingly monopolar and bipolar modes are used.

5. The method of claim 1, wherein the RF generator is switched between a first operating mode, a cutting mode in which the tissue is predominantly cut, and a second operating mode, a coagulation mode, in which the tissue is predominantly coagulated.

6. The method of claim 5, wherein in the coagulation mode the loop is operated in bipolar mode.

7. An RF surgical assembly for RF surgical removal of pathological tissue in hollow organs of a patient, comprising:
- an RF generator configured to generate an RF current, wherein the RF generator has a first output and an antipolar second output;
- a bipolar loop having first and second mutually insulated loop sections which is configured to be brought electrically in contact with the patient; and
- a switchover device operable to switch the RF generator between a bipolar mode and a monopolar mode, wherein:
  - in the bipolar mode, the RF generator connects the first output to the first loop section, and the second output connects to the second loop section such that the RF current flows through the first output and the first loop section, through the patient; and through the second loop section to the second output; and
  - in the monopolar mode, the RF generator connects the first output to at least one of the first loop section and the second loop section, and connects the second output to a neutral electrode which is configured to be attached to the patient, such that the RF current flows through the first output and the at least one of the first loop section and the second loop section, through the patient, and out the neutral electrode to the second output.

8. The device of claim 7, wherein the switchover device includes an adapter which connects a plug contact of a bipolar connecting cable of a bipolar loop to a first contact element which is configured to be plugged into a monopolar RF surgical device.

9. The device of claim 7, wherein the switchover device includes a switch configured to connect the two loop sections to one another and a first double-throw switch configured to connect at least one loop section to the second output.

10. The device of claim 7, wherein the switchover device includes a second double-throw switch for the alternating or for the alternative connection of the first output to the neutral electrode or to at least one loop section.

11. The device of claim 7, wherein the switchover device is electronically controlled.

12. The device of claim 7, wherein the switchover device includes a control device configured to control various operating modes of the RF surgical device.

13. The device of claim 12, wherein the operating modes include at least one of cutting, coagulating, or soft-coagulation.

* * * * *